ional Patent [19]

Hösli

[11] Patent Number: 4,469,788

[45] Date of Patent: Sep. 4, 1984

[54] PROCESS OF IN VITRO DIAGNOSIS OF CYSTIC FIBROSIS

[75] Inventor: Peter Hösli, Paris, France

[73] Assignee: Institut Pasteur, Paris, France

[21] Appl. No.: 346,846

[22] Filed: Feb. 8, 1982

Related U.S. Application Data

[63] Continuation of Ser. No. 154,630, May 30, 1980, abandoned.

[30] Foreign Application Priority Data

Jun. 1, 1979 [FR] France .................................. 79 14234

[51] Int. Cl.³ .......................... C12Q 1/34; C12Q 1/42
[52] U.S. Cl. ...................................... 435/18; 435/21; 435/184
[58] Field of Search ............... 23/230 B; 424/2; 435/4, 435/18, 21, 184

[56] References Cited

U.S. PATENT DOCUMENTS

| 3,002,893 | 10/1961 | Babson | 435/21 |
| 3,902,847 | 9/1975 | Bosch et al. | 422/56 |
| 3,932,221 | 1/1976 | Pfleiderer | 424/2 |

FOREIGN PATENT DOCUMENTS

124680 4/1979 U.S.S.R. .................................. 435/4

OTHER PUBLICATIONS

*Chemical Abstracts*, 89:127224u, "Reliable Diagnosis of the Major Type of Cystic Fibrosis with Fibroblast Cultures", 1978.
*Chemical Abstracts*, 91:155608g, "Cystic Fibrosis: Decreased Thermo-Stability of α Mannosidase in Crude Extracellular Fluids", 1979.
*Chemical Abstracts*, 91:155595a, "Inhibition of Tamm-Horsfall Glyco-Protein Induction of Alkaline Phosphatase in Cystic Fibrosis Fibroplasts", 1979.
Hosli et al., "Cystic Fibrosis: Leakage of Lysosomal Enzymes and of Alkaline Phosphatase into Extracellular Space," *Bio. Chem. & Biophys. Res. Comm.*, Dec., 1977, pp. 741–748.

*Primary Examiner*—Peter A. Hruskoci
*Attorney, Agent, or Firm*—Weiser & Stapler

[57] ABSTRACT

The invention relates to an in vitro process for diagnosing cystic fibrosis, which brings into play conditions, particularly temperatures at which some of the hydrolases released by the cells from the individual under study, particularly α-mannosidase and acid phosphatase, are subject to greater inactivation kinetics, when the cells originated from individuals affected by the disease or capable of transmitting it, than when said cells were from healthy people. The process thus consists of maintaining such cells, either in natural biological media or in culture media at a temperature within said intervals for a time long enough to appreciate the degree or kinetics of inactivation which can then be correlated to the fact that the individual is either healthy or affected by the disease or liable of transmitting it.

4 Claims, 2 Drawing Figures

PROCESS OF IN VITRO DIAGNOSIS OF CYSTIC FIBROSIS

This is a continuation, of application Ser. No. 154,630, filed May 30, 1980 now abandoned.

The cystic fibrosis (also referred to hereafter by the abbreviation "CF"), also named mucoviscidosis, is a most serious autosomal recessive genetic disease, particularly frequent in the populations of European origin. About one child in 2,000–2,500 children is in France affected by this disease. The first signs of this disease appear generally immediately after birth. The most characteristic syndroms consist in the development of chronic pulmonary obstructions, pancreatic deficiencies, a defect in the metabolisation of fats and an extreme sensitivity to infections, particularly at the level of the respiratory tracts. Death follows usually within a few years from the child's birth.

Cystic fibrosis is a family disease which is transmitted according to the recessive autosomal way. It seems today established that children who are likely to be affected by that disease are those whose genetic inheritance results from the chromosomic recombination at the time of fecundation of the genetic inheritances of the father and the mother, when the latter are both carrying a specific chromosomic mutation, yet without being themselves affected by the disease. These parents will be hereafter designated as "CF-heterozygotes". Obviously this expression will also extend to their cells and, more generally, to their own genetic inheritance. Thus those children who will inherit this chromosomic defect from their two parents and who are liable of being affected by the disease will themselves be referred to hereafter as "CF-homozygotes".

It would thus be desirable to have means for detecting this genetic abnormality as soon as possible, since the survival rate of a new-born child potentially affected by the disease would be the best if he could be submitted to early intensive therapy. It would even be better to detect the abnormality in the neonatal phase, wherever possible even in the earliest phase of pregnancy, at a time where a therapeutic interruption of the pregnancy could still be contemplated.

Processes for detecting chromosomic abnormalities on samples of amniotic liquid are already known, when they manifest themselves by visible structural modifications. These techniques are however far more difficult to devise when these abnormalities are not visible and are the expression of future errors in the control or the regulation of the cellular metabolism.

As a matter of fact, the genetic disease which is at the onset of cystic fibrosis seems according to hypotheses which find an ever increasing experimental support, to affect numerous enzymes which take part into the intracellular digestion. Particularly this genetic defect seems to among others affect the lysosomal system with as a result the release of hydrolases in the extracellular spaces, thereby causing multiple intracellular deficiencies of these same hydrolases.

The hypothesis has been proposed concerning more particularly the lysosomal hydrolases, that the genetic defect under consideration affects certain markers carried by these hydrolases, said markers serving to anchor said hydrolases on specific lysosomal membranes receptors. The markers are deemed to be formed of phosphorylated oligosaccharides which are fixed onto the enzymatic proteins by a secondary processing during their passage through the cavities of the endoplasmic reticulum.

The processes of diagnosis known up to this day are difficult to bring into practice and inappropriate for systematic detection of the genetic abnormality under consideration. The process which is most used is the so-called "sweating test", which consists of determining the unusually high reates of sodium and of chlorine which are contained in the sweat of children affected by cystic fibrosis. It is however difficult to bring into practice and requires the patient to be present in the laboratory. Further it can be carried out with a reasonable degree of accuracy as to the results only by very experienced technicians. Obviously it is inappropriate for carrying out neonatal or prenatal detection of cystic fibrosis. Thus up to new processes for néonatal detection have not been developed by reason of the ambiguous results which they produce as well as of the technical difficulties encountered for bringing them into practice.

The invention thus aims at overcoming these difficulties, more particularly at providing a process permitting a diagnosis both easier and safer than the methods known up to this time, which process may be brought into practice by persons who do not have the level of technical competency which is required from the technicians carrying out the "sweat test".

Another object of the invention is to provide a detection test which can be carried out not only in new-born children, or more generally children, but also in embryo, preferably even in the first weeks of pregnancy.

The invention further aims at providing a process enabling the systematic detection at the level of the populations of those individuals who are possible carriers of the genetic defect "CF-heterozygotes". Such systematic diagnosis may for instance be carried out in the course of the prenuptial medical surveys which national legislations often require.

The invention is based on a diffential approach of the behaviours of at least one of the determined enzymes which are likely to take part into the intracellular digestion and to be at least partially affected as a result of a possible genetic defect in the individual from which it originates, whether said individual be "CF-homozygote" or only "CF-heterozygote". For instance it has been found that enzymes originating from a "CF-homozygote" indidual or even from a "CF-heterozygote" exhibited a thermostability more important than that of the same enzyme originating from control individuals whose chromosomes are free of any genetic defect of the type of those which are held responsible of cystic fibrosis.

The invention is based on the determination for each enzyme liable of being taken into consideration, of the limit conditions under which said enzyme will undergo an alteration or inactivation more important when it originates from a "CF-homozygote" or a "CF-heterozygote" individual than when it originates from an individual who does not carry the same genetic defect. The invention is based on the demonstration here reported that one can determine the limit conditions under which the enzyme originating from a normal control remains stable, whereas the same enzyme is liable of undergoing a more or less important degradation depending upon whether it originates from a "CF-homozygote" or a "CF-heterozyote" individual under the same limit conditions.

The process of the invention thus comprises-starting either from a biological medium originating directly from the individual possibly affected by the disease or liable of potentially transmitting the disease, or from a medium of culture or a suspension of cells originating from a culture extraneous to the body previously taken up from that individual—establishing the limit conditions under which the selected enzyme will remain stable or undergo inactivation kinetics but slowed down when it originates from a normal individual, and will be altered or undergo more rapid inactivation kinetics when it originates from a "CF-homozygote" or a "CF-heterozygote" individual; and when said limit conditions have been established, detecting on the sample to be assayed the alteration or more rapid inactivation, if any, of the selected enzyme.

Obviously, these limit conditions can be established once for ever in connection with any selected enzyme. Particularly it will be of advantage to determine the thresholds which will set limits enabling the technician to rapidly determine whether the result of any assayed sample are below or beyond said thresholds, whereby it will be established that in all probability the individual from whom the sample assayed originated was either affected with the disease or capable of transmitting it or healthy.

Particularly, when the parameters taken into consideration consist of inactivation kinetics, it will be of interest to determine threshold ratios separating the different assay results which will be representative of one of the states to be diagnosed; particularly these thresholds may be expressed as percentages of inactivation of the selected enzyme with respect to the assay result obtained in healthy individuals. Thus when this percentage of inactivation is low, particularly lower than a first threshold value it can be concluded to the fact that most probably the tested sample originated from a healthy individual. When the measured ratio exceeds said first threshold but is lower than a second threshold, it may be concluded that the sample originated from an individual who is possibly or certainly a carrier of the genetic defect, and when the assay result is beyond the second threshold, one may conclude to the probability that the sample originated from a "CF-homozygote" individual.

It is understood that the word "individuals" refers to both children and adult persons (particularly "CF-heterozygotes") as well as to embryos, even in the early stages of pregnancy.

In preferred embodiments of the invention, advantage is taken of the existence of a thermolability of the selected enzymes greater when it originates from individuals affected by the disease or liable of transmitting it, than when it originates from healthy people. When thermolability is the determinant parameter, it will be necessary to determine the temperature at which the above said differential behaviours may be observed, particularly the limit temperature above which (or temperature intervals within which) the selected enzyme whose modification is liable of being correlated to the existence of a genetic defect of the type involved in cystic fibrosis is unstable, whereas the corresponding enzyme originating from healthy individuals will remain stable. Other differential parameters than thermostability may be relied upon.

In preferred embodiments of the process of the invention, advantage is taken of the differential thermal behaviours of enzymes such as α-mannosidase or acid phosphatase which have been found to undergo a more rapid inactivation when they originate from "CF-homozygote" individuals or "CF-heterozygote" individuals than when they originate from healthy individuals, at temperatures above 40° C., preferably from 40° C. to 42° C. for α-mannosidase, above 36° C., preferably from 36° to 38° C. for acid phosphatase.

These enzymes are but examples of hydrolases whose nature seems altered by the existence of chromosomic genetic defects in "CF-homozygote" or "CF-heterozygote" individuals. Similar phenomena can be detected in connection with other hydrolases, particularly lysosomal hydrolases, such as α-glucosidase and α-fucosidase.

In the preferred embodiments of the invention mentioned above, the biological samples to be assayed are accordingly subjected to thermal treatments during respectively increasing time intervals, in order to induce the possible appearance of inactivation kinetics of the enzyme studied which will be all the more important as the enzyme will originate from a "CF-homozygote" or a "CF-heterozygote" individual. The biological sample may also consist of any medium previously brought into contact with cells originating from such an individual and in which said cells would then have released the enzyme under consideration.

In the preferred case of α-mannosidase, the temperature of 41° C. is preferred. In case of acid phosphatase the temperature of 36.5° C. is preferred.

A preferred biological medium consists of blood plasma. The fibrinogen and the factors liable of participating to a great extent in the coagulation are preferably removed or totally inhibited.

The initiation of the coagulation phenomena would induce the release by the thrombocytes of thermostable hydrolases the presence of which in the assayed samples would cause the kinetics of thermoinactivation of the thermolabile enzymes to be studied in the in vitro diagnostic test according to the invention to be wholly mistaken.

The inhibition of the coagulation factors may be achieved by means of any appropriate anti-coagulant, for instance heparin.

Any other biological medium can be used to the extent where it will have been brought into contact previously with the cells liable of releasing in that medium the enzymes to be assayed. They may for instance consist of other human biological liquid, for instance urine. Another appropriate biological medium may consist for instance of amniotic liquid taken up from the pregnant woman, said liquid then being liable of containing the cells which are themselves capable of releasing in that medium the enzymes under consideration. These biological media may also consist of the classical media for culturing human cells, for instance fibroblasts.

Preferably, the above-mentioned operations are carried out in said media, the latter being maintained at a pH ranging from 5 to 9, preferably about 7.

It is also further preferred that the assays be performed on very minute amounts of liquid in order to avoid an excess of enzymes in the samples studied and accordingly a possible masking of the phenomena to be observed.

Advantageously, the volumes of the samples of the biological liquid to be treated range from 0.1 to 100 μl.

An important condition for the correct performance of the process of the invention under those circumstances, particularly when it brings into play comparative inactivation kinetics of enzymes, lies in the protection of the thermally treated samples against evaporation.

Advantageously, the reactions are carried out in tubes, the protection against evaporation then being obtained by means of a top oil layer on the sample of biological medium, said oil being selected among those which have densities below 1 and vapour tensions that are extremely low, if not null, at the temperature at which the inactivation tests are to be carried out. Such an oil may for instance consist of paraffin oil.

Any quantitative assaying technique of the enzyme to be studied after said thermal treatments can be resorted to.

It will be particularly advantageous to resort to any of the known techniques which bring into play the action of the enzyme on any one of its substrates, particularly on those the transformation of which can be assayed by photocolorimetric methods. The oil used should then not have fluorescent properties under the contemplated experimental conditions. The non-fluorescent paraffin oil commercialized under the designation UVASOL manufactured by the MERCK Company of DARMSTADT (F.R.G.) may be used with advantage in the preferred process embodiment disclosed hereafter.

The photometric results obtained in the examples hereafter where obtained with a spectrophotofluorimeter PERKIN-ELMER MPF-4.

Other features of the invention will further appear in the course of the following description of preferred examples. Reference will particularly be made in these examples to the drawings in which.

EXAMPLE I

Figure 1:
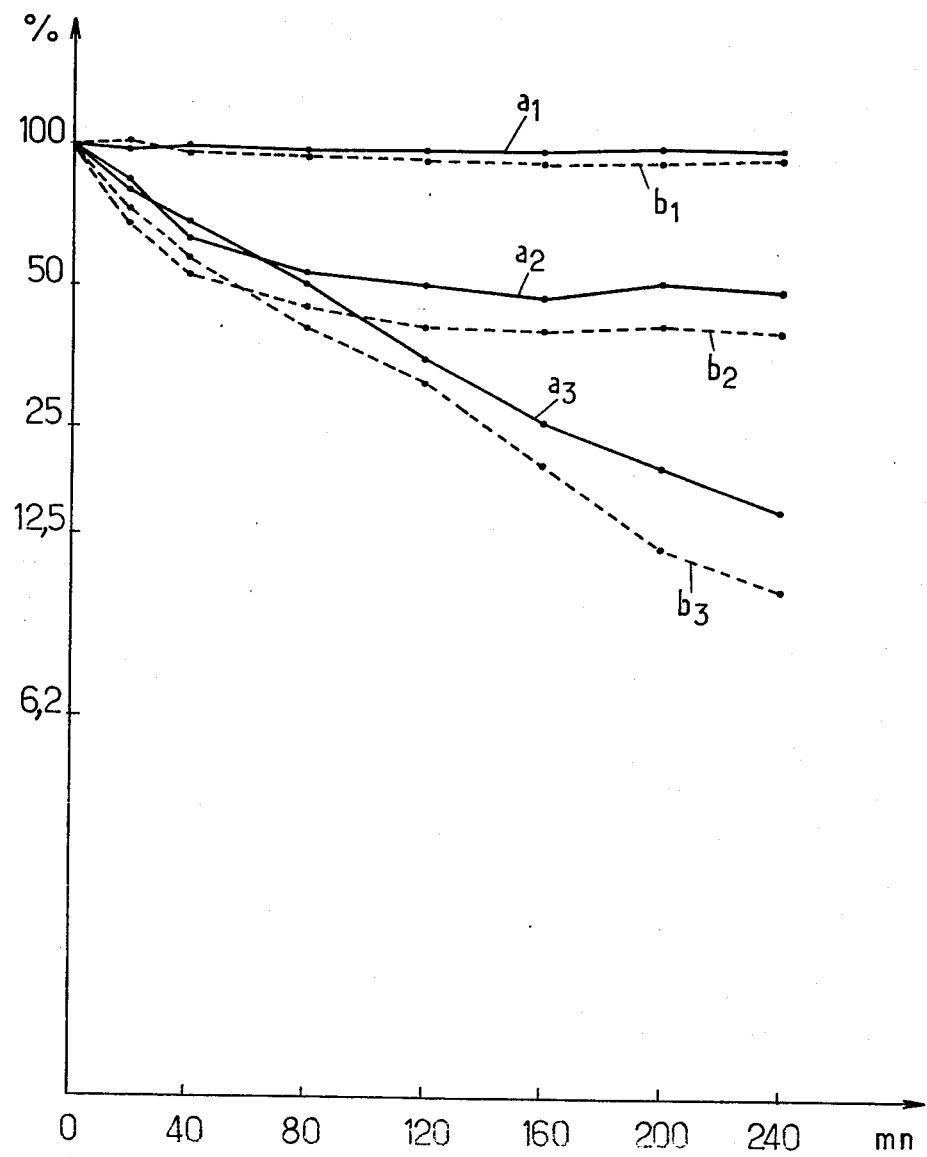
FIG. 1 is representative of the inactivation rate (expressed in % on the axis of ordinates) of the assayed enzymes in samples of blood plasma as defined above, as a function of increased durations of thermal inactivation (expressed in minutes on the axis of abscisses), these enzymes originating from healthy, "CF-homozygote" and "CF-heterozygote" individuals respectively.

Venous blood was drawn into plastic tubes containing exactly 25 I.U. of heparin per ml of blood, put into ice water and processed in one hour at the latest. For separation of plasma and blood cells the tubes were sequentially centrifuged with swing-out-beakers in a 4° C. refrigerated centrifuge, first for five minutes at 400 g and subsequently for ten minutes at 3,000 g. Plasma aliquots were then distributed into Eppendorf tubes, frozen and stored in liquid nitrogen until experimental use. Aliquots, thawed up in ambient air, must be immediately used and should under no circumstances be refrozen.

The following technique, employing disposable Eppendorf tubes, has been developed for sequential heat inactivation and enzyme assay of small plasma samples. The essential point was to protect the small incubation volume during heat-inactivation and enzyme assay against evaporation by covering the sample with nonfluorescent paraffin oil UVASOL. After each pipetting the oil is forced to cover the upper surface of the incubation sample by centrifugation of the Eppendorf tubes for 20 seconds in the centrifuge at 6,000 g.

For the enzyme assays 10 µl of enzyme sample were incubated with 10 µl of 10 mM 4-Methylumbelliferyl-α-D-mannopyranoside (or 10 µl of 11 mM 4-Methylumbelliferylphosphate, respectively) in 0.1M Citrate buffer, pH 5.4 for 90 minutes at 30° C. After incubation, 1 ml of 0.5M carbonate buffer, pH 10.7, was added for fluorescence reading in the spectrophotofluorimeter, with an excitation wave length 360 and an emission wave length 448 mµ.

The following procedure, where each heat-inactivation and enzyme assay was done in triplicate has been employed:

1. Plasma samples were thawed up in ambient air, prediluted 1:10 with 0.9% NaCl, and kept in ice water until heat-inactivation.
2. 10 µl samples of prediluted plasma were distributed into Eppendorf tubes.
3. 25 µl of Uvasol oil was added to each of the tubes which were then centrifuged for 20 seconds at 6,000 g. This step enables an oil layer to be formed, which protects the plasma sample against evaporation, in the course of the subsequent heat inactivation step.
4. Heat inactivation was carried out in a water-bath from 0 to 240 minutes at 41° C. for α-mannosidase and at 36.5° C. for acid phosphatase. The starting times of the thermal inactivation treatments carried out on the different tubes were respectively shifted from one another in order to enable the desired durations of the thermal treatments in the different tubes to end substantially at the same time.
5. All samples were stopped simultaneously by putting them for 5 minutes into an ice water-bath.
6. 10 µl of enzyme substrate was added to each tube and
5. the tubes were recentrifuged for 20 seconds at 6,000 g in order to achieve whenever necessary the transfer of the substrate through the oil layer and its bringing into contact with the plasma samples to be assayed.
7. The samples were then incubated in a water-bath for 90 minutes at 30° C.
8. All samples were stopped simultaneously by putting them for 5 minutes into an ice water-bath.
9. All samples were then diluted with 1 ml of carbonate buffer, pH 10.7 recentrifuged for 20 seconds at 6,000 g and read in conventional quartz cuvettes with the spectrophotofluorimeter.

The observed results will be commented hereafter, together with those obtained on cultures of skin cells obtained from healthy individuals, "DF-homozygote" patients and "CF-heterozygote" carriers.

EXAMPLE II

Fibroblast cell cultures were obtained in conventional ways from skin biopsies of normal controls, CF-patients and CF-heterozygotes (carriers), and kept for three days at 37° C. in confluency in a growth medium consisting of HAM FIO (GIBCO) supplemented with 15% FCS (GIBCO). After washing, the growth medium was replaced for two days with a collection medium (2.2 ml HAM F10, supplemented with 5% FCS which had been previously heat-inactivated for three hours at 56° C.). The collection medium was then cleared by two minute centrifugation, 5,000 g. Aliquots of this medium were distributed into Eppendorf tubes, frozen and stored in liquid nitrogen until experimental use. Thawed aliquots must be immediately used and cannot be refrozen.

The collection media so obtained were subjected to the assay procedure described in steps 1 to 9, except for the duration of incubation of step 6° which has been extended to 180 minutes.

FIG. 1 is representative of the results which were obtained on the study of the thermal inactivation curves of α-mannosidase (curves $a_1$, $a_2$, $a_3$) on the one hand and of acid phosphatase (curves $b_1$, $b_2$, $b_3$) carried out on plasma samples assayed according to the conditions set forth hereabove in connection with example I.

Curves $a_1$, $b_1$ were obtained from a blood sample originating from a healthy control, curves $a_2$, $b_2$ are illustrative of the results obtained on a plasma originating from an obligate "CF-heterozygote" (one of the parents of a child affected with cystic fibrosis).

Finally, curves $a_3$, $b_3$ illustrate the results obtained on a plasma sample originating from a "CF-homozygote" individual.

The curves of FIG. 1 show that, under the operating condition described, the α-mannosidase and acid-phosphatase enzymes do not practically undergo any inactivation.

To the contrary, there is observed in connection with the "CF-heterozygotes" (curves $a_2$, $b_2$) a partial inactivation during the first 80 minutes of those of the samples which have been subjected to the thermal inactivation treatment, this inactivation remaining partial as shown by the curves $a_2$, $b_2$, which become flat at a level approximating 50% for those of the samples which are subjected to the thermal inactivation treatment over longer periods of time (80 to 240 minutes).

Finally, it was observed for the "CF-homozygote" individuals an inactivation which increased with the length of the inactivation treatment up to a zero-activity which is attained after a prolonged duration of the inactivation treatment.

Figure 2:
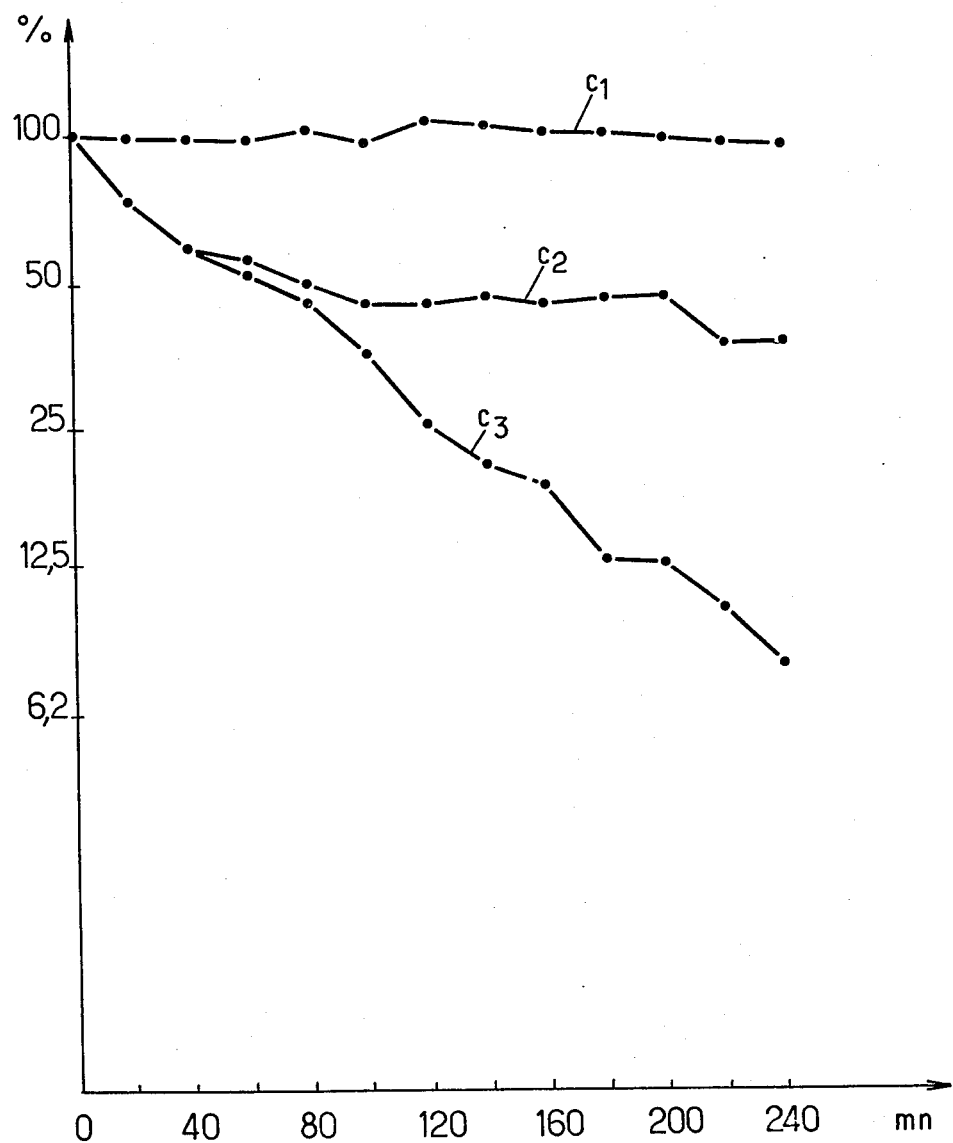
FIG. 2 represents the variations of the same phenomena under the same conditions with respect to enzymes contained in the supernatants of media in which the cells originating from healthy, "CF-homozygote" and "CF-heterozygote" individuals were previously cultivated.

FIG. 2 is representative of the results obtained from the collection media originating from the cellular cultures themselves obtained from the same healthy controls (curves $c_1$), the obligate "CF-heterozygote" (curve $c_2$) and the "CF-homozygote" individuals (curve $c_3$).

The behavior of the enzyme assayed in example II (α-mannosidase) is substantially the same as that of the blood plasma samples of example I.

The results obtained on series of individuals belonging to the above-mentioned three categories are reported in tables 1a, 1b and 1c.

The numbers shown in these different tables correspond to the percentages of the residual activities of α-mannosidase and acid-phosphotase after the thermal inactivation treatment under the conditions set forth in Example I in samples of plasma originating from the different donors, after they were maintained at temperatures of 41° C. and 36.5° C. respectively over periods of 40 minutes, 120 minutes and 200 minutes respectively, as compared to the activities assayed for the same enzymes in samples which were not subjected to said thermal inactivation and which were to the contrary maintained over the corresponding periods in ice bath.

The results of table 1a are those obtained on plasmas of 20 healthy individuals. In the same manner the table 1b reports the results obtained on plasmas originating from 22 obligate "CF-heterozygote" individuals. Finally the results reported in table 1c are those obtained on blood plasmas obtained from 5 "CF-homozygote" individuals.

The mean results with standard deviations (S.D.) are also reported in those tables.

The results appearing in tables 1a, 1b, 1c show that the results are substantially reproducible in the different individuals of a same group. It will thus be understood that upon running the test according to the conditions which have been disclosed in EXample I, it can be reasonably inferred that when applying the diagnosis test according to the invention to the blood plasma of any individual, an inactivation percentage in proportion beyond 75–95% after 200 minutes of thermal inactivation treatment at 41° C. (for α-mannosidase), enables one to reach the conclusion that the individual under consideration was most probably a "CF-homozygote". When the observed percentage of inactivation is of the order of 40–60% after 200 minutes of the treatment, it can be concluded that the blood samples under test originated from a "CF-heterozygote" individual. An inactivation of the order of from 25 to 35% witnesses a likely hood, if not of a certainty, of the individual under test being a "CF-heterozygote" carrier.

Thus the process of the invention may also be termed as a process for the in vitro diagnosis of cystic fibrosis based on the differential behaviour of an enzyme selected from among the enzymes which are likely to take part into the intracellular digestion and to be affected at least partially as a result of a possible genetic defect correlated to cystic fibrosis in the individual from whom it originates, which comprises—starting either from a biological medium originating directly from the individual possibly affected by the disease or liable of potentially transmitting the disease, or from a medium of culture or a suspension of cells originating from a culture extraneous to the body previously taken up from that individual—measuring in said medium the degree of alteration or of inactivation, if any, of the selected enzyme and comparing it to predetermined thresholds enabling the measured degree of alteration or inactivation to be correlated to a state of normality, to a "CF-heterozygote" state or to a "CF-homozygote" state of the individual from whom said sample originated.

TABLE 1a

THERMAL INACTIVATION OF α- MANNOSIDASE/ACID PHOSPHATASE (in percentage)

| Normal controls | 0' | 40' | 120' | 200' |
|---|---|---|---|---|
| 1 | 100/100 | 99/97 | 99/96 | 99/94 |
| 2 | 100/100 | 97/99 | 98/99 | 99/93 |
| 3 | 100/100 | 97/96 | 96/99 | 87/93 |
| 4 | 100/100 | 99/98 | 97/92 | 97/91 |
| 5 | 100/100 | 84/94 | 85/94 | 87/91 |
| 6 | 100/100 | 95/95 | 96/93 | 95/92 |
| 7 | 100/100 | 95/99 | 94/95 | 94/94 |
| 8 | 100/100 | 97/96 | 98/95 | 96/93 |
| 9 | 100/100 | 99/104 | 97/101 | 96/92 |
| 10 | 100/100 | 97/100 | 94/91 | 100/94 |
| 11 | 100/100 | 98/101 | 100/102 | 100/91 |
| 12 | 100/100 | 103/93 | 104/87 | 103/94 |
| 13 | 100/100 | 106/103 | 95/98 | 100/98 |
| 14 | 100/100 | 98/102 | 94/99 | 91/97 |
| 15 | 100/100 | 97/101 | 94/101 | 92/100 |
| 16 | 100/100 | 97/105 | 95/99 | 95/105 |
| 17 | 100/100 | 99/94 | 102/91 | 100/90 |
| 18 | 100/100 | 99/98 | 93/99 | 86/97 |
| 19 | 100/100 | 99/100 | 94/98 | 92/88 |
| 20 | 100/100 | 98/97 | 94/98 | 84/97 |
| Mean value ± | 100/100 | 97.7/98.6 | 96/96 | 94.7/94.2 |

TABLE 1a-continued

THERMAL INACTIVATION OF α- MANNOSIDASE/
ACID PHOSPHATASE (in percentage)

| Normal controls | 0' | 40' | 120' | 200' |
|---|---|---|---|---|
| S.D. | | ±4.0/±3.4 | ±3.9/±4.0 | ±5.4/±3.9 |

(S.D. = Standard Deviation).

TABLE 1b

THERMAL INACTIVATION OF α- MANNOSIDASE/
ACID PHOSPHATASE (in percentage)

| CF-heterozygotes | 0' | 40' | 120' | 200' |
|---|---|---|---|---|
| 1 | 100/100 | 66/71 | 45/45 | 46/48 |
| 2 | 100/100 | 64/56 | 55/47 | 51/50 |
| 3 | 100/100 | 63/56 | 50/41 | 50/41 |
| 4 | 100/100 | 67/69 | 56/50 | 55/48 |
| 5 | 100/100 | 66/58 | 58/52 | 54/49 |
| 6 | 100/100 | 68/53 | 58/42 | 53/39 |
| 7 | 100/100 | 80/69 | 53/50 | 55/45 |
| 8 | 100/100 | 72/68 | 49/49 | 44/45 |
| 9 | 100/100 | 75/79 | 55/56 | 51/46 |
| 10 | 100/100 | 73/76 | 47/53 | 50/53 |
| 11 | 100/100 | 86/77 | 53/41 | 51/41 |
| 12 | 100/100 | 84/70 | 53/40 | 50/44 |
| 13 | 100/100 | 79/77 | 57/49 | 50/48 |
| 14 | 100/100 | 75/76 | 49/46 | 50/49 |
| 15 | 100/100 | 79/70 | 50/39 | 50/40 |
| 16 | 100/100 | 79/71 | 49/45 | 45/41 |
| 17 | 100/100 | 81/68 | 55/47 | 53/48 |
| 18 | 100/100 | 74/72 | 56/37 | 52/28 |
| 19 | 100/100 | 88/63 | 55/38 | 56/44 |
| 20 | 100/100 | 75/67 | 48/42 | 52/46 |
| 21 | 100/100 | 85/75 | 56/48 | 54/46 |
| 22 | 100/100 | 79/83 | 47/47 | 45/44 |
| mean value ± | 100/100 | 75.4/69.3 | 52.5/45.6 | 50.7/44.7 |
| S.D. | | ±7.4/±8.0 | ±4.1/±5.1 | ±3.4/±5.2 |

TABLE 1c

THERMAL INACTIVATION OF α- MANNOSIDASE/
ACID PHOSPHATASE (in percentage)

| CF-homozygotes | 0' | 40' | 120' | 200' |
|---|---|---|---|---|
| 1 | 100/100 | 57/59 | 29/25 | 11/6 |
| 2 | 100/100 | 62/58 | 32/29 | 16/7 |
| 3 | 100/100 | 68/56 | 37/34 | 22/14 |
| 4 | 100/100 | 68/72 | 40/40 | 19/15 |
| 5 | 100/100 | 65/56 | 45/27 | 26/9 |
| Mean ± | 100/100 | 64/60 | 36.6/31 | 18.8/10.2 |
| S.D. | | ±4.6/±6.7 | ±6.3/16.0 | ±5.7/±4 |

I claim:

1. A process for the in vitro diagnosis of cystic fibrosis based on the stability of α-mannosidase which is affected by a genetic defect related to cystic fibrosis and which is less stable thermally when it originates from individuals having said genetic defect than when it originates from individuals without said genetic defect, and wherein the degree of thermal inactivation at a temperature of 41° C. and at neutral pH of said α-mannosidase from individuals with said genetic defect relative to the degree of thermal inactivation at 41° C. of said α-mannosidase from individuals without said genetic defect has been predetermined, comprising obtaining a sample of said α-mannosidase originating from an individual to be diagnosed for said genetic defect;

measuring the degree of thermal inactivation of said α-mannosidase sample at a temperature of about 41° C. and at a neutral pH;

comparing the degree of inactivation of said sample of α-mannosidase with the predetermined degrees of inactivation of said α-mannosidase originating from an individual without said genetic defect and from said individual having said genetic defect to determine whether the individual being diagnosed has said genetic defect.

2. The process of claim 1 wherein the said α-mannosidase is less stable thermally when it originates from CF-heterozygotes than when it originates from an individual without said genetic defect and which is further less stable when it originates from CF-homozygote individuals, than when it originates from heterozygote individuals and wherein the degree of thermal inactivation of said α-mannosidase at a temperature of 41° C. and at a neutral pH of said α-mannosidase from individual with said genetic defect relative to the degree of inactivation at 41° C. of said α-mannosidase from CF-heterozygote individuals has been predetermined, and further wherein the degree of thermal inactivation at 41° C. of said α-mannosidase originating from CF-homozygote individuals relative to the degree of thermal inactivation at 41° C. of CF-heterozygote individuals has been predetermined too, comprising comparing the degree of inactivation resulting from said measurement relative to the degree of inactivation respectively of said α-mannosidase from CF-homozygote individuals, of said α-mannosidase of said CF-heterozygote individuals, of said α-mannosidase from individuals without any of said genetic defects to determine whether the individual diagnosed is a CF-heterozygote or a CF-homozygote.

3. A process for the in vitro diagnosis of cystic fibrosis based on the stability of acid phosphatase which is affected by a genetic defect related to cystic fibrosis, and which is less stable thermally when it originates from individuals having said genetic defect than when it originates from individuals without said genetic defect, and wherein the degree of thermal inactivation at a temperature of 36.5° C. and at a neutral pH of said acid phosphatase from individuals with said genetic defect relative to the degree of thermal inactivation at 36.5° C. of said acid phosphatase from individuals without said genetic defect has been predetermined, comprising obtaining a sample of said acid phosphatase originating from an individual to be diagnosed for said genetic defect;

measuring the degree of thermal inactivation of said acid phosphatase sample at a temperature of about 36° C. and at a neutral pH.

comparing the degree of inactivation resulting from said measurement relative to the degrees of inactivation respectively of said acid phosphatase from individuals with said genetic defect and from individuals without said genetic defect, to determine whether the individual being diagnosed has said genetic defect.

4. The process of claim 3 wherein the said acid phosphatase is less stable thermally when it originates from CF-heterozygotes than when it originates from an individual without said genetic defect and which is further less stable when it originates from CF-homozygote individuals than when it originates from heterozygote individuals, and wherein the degree of thermal inactivation of said acid phosphatase at a temperature of 30.5° C. of said acid phosphatase from individuals with said genetic defect relative to the degree of inactivation at 36.5° C. of said-mannosidase from CF-heterozygote individuals has been predetermined, and further wherein the degree of thermal inactivation at 36.5° C. and at a neutral pH of said acid phosphatase originating from CF-homozygote individuals relative to the degree of thermal inactivation at 36.5° C. of CF-heterozygote individuals has been predetermined too, comprising:

comparing the degree of inactivation resulting from said measurement relative to the degree of inactivation respectively of said acid phosphatase from CF-heterozygote individuals of said acid phosphatase of said CF-heterozygote individuals and of said acid phosphatase from individuals without any of said genetic defects to determine whether the individual diagnosed is a CF-heterozygote or a CF-homozygote individual.